United States Patent [19]

Sircar

[11] 4,171,207
[45] Oct. 16, 1979

[54] SEPARATION OF MULTICOMPONENT GAS MIXTURES BY PRESSURE SWING ADSORPTION

[75] Inventor: Shivaji Sircar, Allentown, Pa.

[73] Assignee: Air Products and Chemicals, Inc., Allentown, Pa.

[21] Appl. No.: 935,424

[22] Filed: Aug. 21, 1978

[51] Int. Cl.² ............................................. B01D 53/04
[52] U.S. Cl. ......................................... 55/26; 55/58; 55/62; 55/75
[58] Field of Search ................... 55/20, 21, 25, 26, 33, 55/58, 62, 68, 74, 75, 179, 387, 389

[56] References Cited

U.S. PATENT DOCUMENTS

| | | | |
|---|---|---|---|
| 2,918,140 | 12/1959 | Brooks | 55/58 |
| 3,102,013 | 8/1963 | Skarstrom | 55/62 X |
| 3,150,942 | 9/1964 | Vasan | 55/33 X |
| 3,176,444 | 4/1965 | Kiyonaga | 55/26 |
| 3,221,476 | 12/1965 | Meyer | 55/179 X |
| 3,282,647 | 11/1966 | Skarstrom et al. | 55/33 X |
| 3,733,775 | 5/1973 | Barrere, Jr. | 55/62 X |
| 4,042,349 | 8/1977 | Baudouin et al. | 55/25 |
| 4,077,779 | 3/1978 | Sircar et al. | 55/25 |

Primary Examiner—Robert H. Spitzer
Attorney, Agent, or Firm—Ronald B. Sherer; E. Eugene Innis; Barry Moyerman

[57] ABSTRACT

Multicomponent gas mixtures containing (1) hydrogen as primary component, (2) a secondary key component that is more strongly sorbed by the adsorbent than hydrogen and (3) one or more dilute components more strongly sorbed than both hydrogen and the secondary key component, are subjected to selective adsorption in a pressure swing cyclic adsorption system for the separate recovery of high purity hydrogen and of the secondary component. A given example is the treatment of effluent gas from a hydrodesulfurization plant after removal of the sulfur, wherein hydrogen and methane are separately recovered substantially freed of $C_2+$ hydrocarbons present in such effluent gas.

22 Claims, 1 Drawing Figure

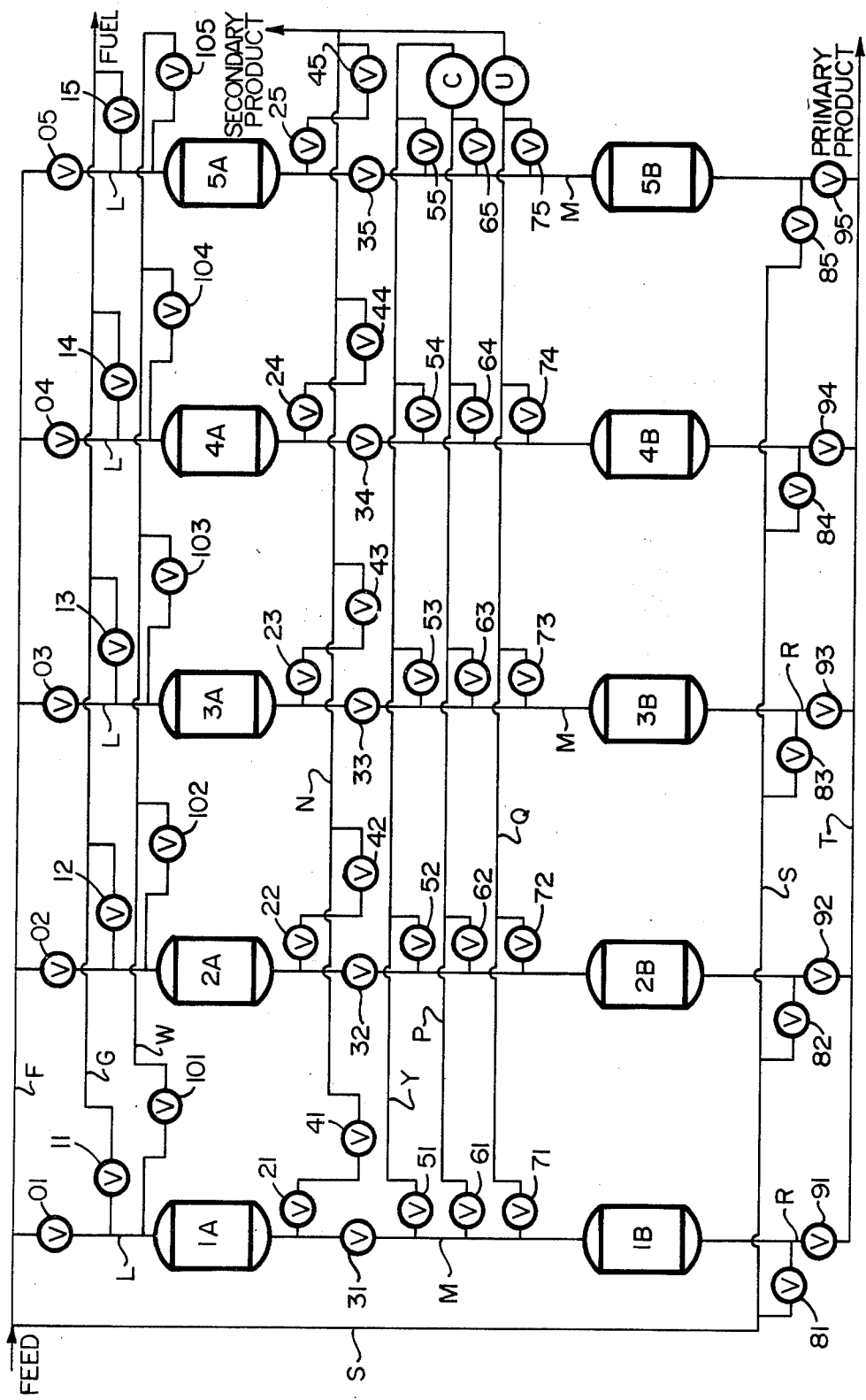

SEPARATION OF MULTICOMPONENT GAS MIXTURES BY PRESSURE SWING ADSORPTION

RELATED APPLICATION

The present application is related to Applicant's companion application Ser. No. 935,435 filed of even date herewith entitled Separation of Multicomponent Gas Mixtures (Attorney's Docket No. 211-P-US02199).

BACKGROUND OF THE INVENTION

1. Field of the Invention

This invention relates generally to separation of gaseous mixtures by selective adsorption and is more particularly concerned with a pressure swing adsorption system designed and operated for separate recovery from a multicomponent gas mixture of a primary key component and a secondary key component, each substantially freed of other dilute components present in the original gas mixture subject to treatment. To effect such separate recovery of desired components from the feed gas mixture the system of the invention uses separate beds of adsorbent in series gas flow therebetween during the adsorption stage, yet designed to be regenerated separately, using different regeneration or desorption procedures. Most particularly, the invention is chiefly concerned with the separate recovery of hydrogen and methane from gas mixtures including these components in addition to $C_2$ and higher hydrocarbons.

2. Prior Art

Pressure swing cyclic adsorption systems designed for fractionation of gaseous mixtures by selective adsorption are well known in the art. In these systems one or more desired components of the feed gas mixture are separately recovered at a yield and purity depending upon the efficiency of the designed operation.

Illustrative of typical systems indicated to be especially useful in the recovery of hydrogen from gaseous mixtures with $CH_4$ and/or $CO_2$ are those described in U.S. Pat. Nos. 3,138,439; 3,142,547; 3,788,037. Other patents describe in general systems for separation of essentially binary gas mixtures or of multicomponent gas mixtures, asserted to be applicable in recovery of hydrogen from such mixtures. Illustrative of these are the systems described, for example, in U.S. Pat. Nos. 3,221,476; 3,430,418 and 3,720,042. Also among the systems described in the prior patent art are those employing separate adsorbent beds operated in series flow and designed for, or stated to be applicable in, separate recovery of hydrogen and one or more other components present in a multicomponent feed gas mixture. Typical among such systems are those described in U.S. Pat. Nos. 3,102,013; 3,149,934; 3,176,444; 3,237,379; 3,944,400 and 4,000,990.

Among the various prior art patents relating to pressure swing adsorption, the recovery of hydrogen from multicomponent gas streams also containing methane and higher hydrocarbons is particularly disclosed in U.S. Pat. Nos. 3,102,013; 3,142,547 and 3,176,444.

In U.S. Pat. No. 4,077,779, there are described adsorption systems designed primarily for separation of binary gas mixtures which may contain trace amounts of other impurities. While the systems therein described can be satisfactorily operated in separation of such binary gas mixtures, these systems cannot be efficiently utilized in the treatment of multicomponent gas mixtures containing in addition to two major key components a certain quantity (more than trace amounts) of one or more dilute contaminants. The presence of such dilute components adversely affects the efficiency of gas separation by pressure swing adsorption techniques designed for handling essentially binary gas mixtures.

In typical multicomponent gas mixtures confronted in industry for desired separation and recovery therefrom of desired components there are generally present two bulk key components accompanied by a certain quantity of dilute impurities. One of the key components, generally present in predominant quantity, consitutes the desired primary product, which can be separated and recovered at high purity by pressure swing adsorption. The remaining bulk component is recoverable as a secondary product. The other dilute constituent gases present in said multicomponent gas mixtures are usually of such nature and/or present in such amount that there is little incentive for their separate recovery in enriched form. An impure stream of these dilute components or their presence in the recovered secondary product is often acceptable.

Multicomponent gas mixtures generally encountered in industrial gas separation can be classified into two different groups:

(1) Such mixtures in which the minor dilute components are less strongly adsorbed than the secondary key component by the adsorbent chosen for the process.

(2) Such mixtures in which the minor diluent components are more strongly adsorbed than the secondary key component.

An example of a mixture of the first type is the gaseous effluent from a shift converter in a hydrocarbon reforming plant. A typical composition of such effluent may be 76% $H_2$, 20% $CO_2$, 3.5% $CH_4$ and 0.5% CO (each by volume). From such mixture $CO_2$ is to be removed and hydrogen recovered as primary component in substantially pure state. The dilute impurities, CO and $CH_4$ are less strongly sorbed than $CO_2$ on most commercial sorbents such as activated carbon and molecular sieves.

An example of a mixture of the second type is the effluent gas from a hydrodesulfurization plant, wherein it is desired to remove $CH_4$ to recover high purity hydrogen for recycle. A typical hydrodesulfurization plant effluent gas after removal of the sulfur compounds may contain 65% $H_2$, 20% $CH_4$, and 5% each of $C_2$, $C_3$ and $C_4$–$C_6$ hydrocarbon components (each by volume). In this instance also, hydrogen constitutes the primary component. The dilute $C_2+$ hydrocarbons are usually more strongly sorbed than the secondary component ($CH_4$) on most commercial sorbents.

The present invention is particularly concerned with the separation of multicomponent gas mixtures of the second type hereinabove described. The primary requirement for separation of such gas mixtures is that the hydrogen be recovered at high purity and at high yield so that it can be recycled efficiently to the desulfurization plant.

This requirement can be successfully met by practice of the present invention. In addition, the present invention provides an opportunity to produce a secondary product stream containing substantially pure $CH_4$ along with a tertiary product stream containing the $C_2+$ hydrocarbons, some $CH_4$ and some $H_2$. This offers a choice to the user who may prefer to utilize the $CH_4$ byproduct stream elsewhere instead of using it as fuel for economic reasons. The tertiary product stream can be used as a fuel gas.

SUMMARY OF THE INVENTION

In practice of the pressure swing adsorption method according to the invention, a plurality of trains of adsorbent beds are operated in parallel and in timed sequence, each such train comprising a first adsorbent bed containing an adsorbent selective for preferential retention of the more strongly sorbed dilute components of a multicomponent gas stream (such as $C_2+$ hydrocarbons in preference to methane and hydrogen in the illustrated example) and a second adsorbent bed in series flow communication with said first bed and containing an adsorbent effective in selective retention of the secondary key component (such as methane in the illustrated example) permitting the primary key component (such as hydrogen in the illustrated example) to pass through the bed essentially unadsorbed. Each train of adsorbent beds undergoes in its turn during a cycle the following sequence of steps:

1. Adsorption. The feed gas mixture at superatmospheric pressure is passed through a train of two adsorbent beds in series, with the withdrawal from the second bed outlet of an unadsorbed effluent comprising high purity primary key product (hydrogen).

2. Switch Adsorption. At the end of step 1, series flow communication between said first and second adsorbent beds of the train is cut off and the flow of the feed gas mixture is switched to another train in the system which is thus placed on the adsorption step of the cycle, such other train having been previously brought to the desired superatmospheric feed pressure. While such adsorption step is going on in the other train, the initial train that has completed the adsorption step undergoes the following operations:

2a. High pressure rinse. The second bed of the first train is subjected to rinsing with an essentially pure stream of the secondary key product (methane), and simultaneously the first bed of that train is subjected to 2b. Pressure equalization; whereby the first bed of the first train is brought to an intermediate pressure level by withdrawal of gas therefrom, followed by 2c. Depressuring; wherein further gas is withdrawn from that first bed to bring the same to substantially ambient pressure level while discharging the effluent gases during this step as part of the tertiary product gas ($H_2$, $CH_4$ and $C_2+$ hydrocarbons).

3a. Depressuring. The second bed of the first train after completion of step (a) is depressurized to substantially ambient pressure level. Part of the effluent gas during this step is recompressed to about the feed pressure level and recycled as the high pressure rinse gas to another second bed in the train then undergoing step 2a. Yet another part of the effluent gas is utilized in 3b. Ambient pressure rinse; wherein the effluent from step 3a is passed through the first bed of the first train at near ambient pressure while discharging the effluent from the said first bed as part of the tertiary product gas.

4a. Evacuation. The second bed of the first train at the end of step 3a is further depressurized to a subatmospheric pressure level. The evacuation effluent gas is withdrawn as secondary key product.

4b. Optional ambient pressure rinse. A part of the evacuation effluent from step 4a may be employed to further rinse the first bed of the first train if that bed had not been sufficiently cleaned in the previous ambient pressure rinse step (3b).

5a. Repressuring. At the end of step 4a, the evacuated second bed of the first train is repressurized to the initial feed pressure level with primary product gas.

5b. During such repressuring of the second bed of the first train, the first bed of that train is separately pressurized to an intermediate pressure level by flow of gas thereto from the first bed of another train then undergoing step 2b to bring the thus interconnected beds to equal pressure.

5c. While repressuring of the second bed of the first train is continued flow communication between the second and first beds of the first train is reestablished and primary product gas is introduced into the first bed thus bringing both beds of the first train to initial feed pressure level for start of a new cycle with step 1.

By operation in the manner described in the foregoing outlined sequence, there is obtained:

(1) Recovery of the primary product ($H_2$) as a stream of high purity.

(2) High recovery of the primary product.

(3) Recovery of a secondary product stream ($CH_4$) of high purity.

(4) Continuous introduction of the feed gas into the separation system and continuous withdrawal of the primary, the secondary and the tertiary product streams.

(5) Continuous operation of the compressors and the vacuum pumps.

The operation of the invention will be fully understood and certain of its advantages appreciated from the detailed description which follows read with the accompanying drawing illustrating a practical embodiment of a preferred system in which the invention may be practiced.

The single FIGURE of drawing is a flow diagram of a preferred embodiment employing five trains of adsorbent vessels each train having a first bed of adsorbent and a second bed of adsorbent which can be placed in series flow communication.

DETAILED DESCRIPTION

Referring now to the drawing, the first group of vessels or adsorption columns are labeled respectively 1A, 2A, 3A, 4A, 5A. The second group of companion vessels are labeled respectively 1B, 2B, 3B, 4B, 5B. The feed gas to be separated may be delivered to a selected initial column of the A group from a feed gas manifold F by opening the appropriate one of the valves 01, 02, 03, 04 or 05 which permit flow communication between the manifold F and the inlet end of the A vessels through the connecting gas lines L. Lines L are also connected to two other manifolds G and W through the valve sets 11, 12, 13, 14, 15 and 101, 102, 103, 104, 105 respectively. Gas can be selectively withdrawn out of the system from the A vessels through the manifold G by appropriate openings of the valves 11, 12, 13, 14, 15. Manifold W can be used to pressure equalize two A vessels by appropriately opening the valves from the sets 101, 102, 103, 104, 105.

At the outlet end of each of the A vessels there is a gas flow line M serving as a gas flow connection between an A vessel and a companion B vessel of each train. Series flow communication between an A vessel and its companion B vessel can be established by opening the appropriate valves 31, 32, 33, 34 or 35 which are mounted on the M lines. Each of the M lines is also connected to four other gas manifolds N, Y, P and Q. The manifold N can be selectively connected to either of the A vessels by selective opening of one or more of the valves from the sets 21, 22, 23, 24, 25 and 41, 42, 43, 44, 45. Similarly, the manifold Y can be selectively connected to either of the B vessels by selective opening of one or more of the control valves from the sets 51, 52, 53, 54, 55. The manifold P can be selectively connected with one of the B vessels by appropriate opening of the valves from the set 61, 62, 63, 64, 65. The manifold Q can be selectively connected to one of the B vessels by opening appropriate valves from the set 71, 72, 73, 74, 75.

At the outlet end of each of the B vessels, there is a gas line R. The R lines can be connected to two different gas manifolds S and T selectively by selective openings of the valves of the sets 81, 82, 83, 84, 85 and 91, 92, 93, 94, 95 respectively. The manifold S is also connected to the feed line F. Valves 91, 92, 93, 94, 95 can be opened to withdraw gas from the B vessels into the T manifold. They can also be used to introduce gas into the B vessels from the manifold T.

The manifold P is also connected to the inlet end of a compressor C. The manifold Y is connected to the exit end of the compressor. The manifold Q is connected to the inlet of a vacuum pump U. The manifold N is connected to the exit end of the vacuum pump. Thus, gas can be withdrawn from one of the B vessels through the manifold P by opening an appropriate valve from the sets 61, 62, 63, 64, 65 and compressed by the compressor C. The compressed gas can be sent to another B vessel through the Y manifold by opening one of the valves in the set 51, 52, 53, 54, 55. Similarly, gas can be withdrawn from one of the B vessels by evacuation through the Q manifold by opening one of the valves from the set 71, 72, 73, 74, 75. The evacuated gas, after compressing to near ambient pressure in the vacuum pump, can be withdrawn from the system or sent to one of the A vessels through the N manifold by opening the appropriate valves from the sets 41, 42, 43, 44, 45 and 21, 22, 23, 24, 25. While the flow diagram shows evacuation of the B vessels at the feed inlet end of such vessels, it will be understood that evacuation can be effected at an intermediate level of the vessel.

During the first step of the process wherein the feed gas mixture to be separated is passed through an A vessel and a B vessel, connected in series, for selective removal of the secondary and the tertiary components of the mixture, this is achieved by selective openings of the valves from the sets 01, 02, 03, 04, 05; 31, 32, 33, 34, 35 and 91, 92, 93, 94, 95. For example, if the feed gas is introduced into the vessels 1A and 1B, valves 01, 31 and 91 are opened. This way the tertiary components of the feed mixture are selectively removed by the adsorbent in the 1A vessel, and most of the unadsorbed primary and secondary components pass into the 1B vessel through the valve 31. The secondary component is then selectively removed by the adsorbent in 1B vessel permitting a stream of essentially pure primary component flow out of the B vessel through valve 91 and the primary product of manifold T. The entire sequence of the process steps carried out in the illustrated embodiment employing five trains of vessels, each train comprising an A vessel and a B vessel is hereinafter outlined. The description is particularly addressed to the separation of hydrogen (primary product) from a mixture comprising methane (secondary component) and $C_2+$ hydrocarbons (tertiary components):

1. Adsorption: The feed gas mixture is passed in series through a selected train of adsorbent columns (say 1A and 1B) which were previously brought to superatmospheric feed gas pressure. Valves 01, 31 and 91 are opened during this step. The adsorption step is continued until the secondary key component ($CH_4$) breaks through the exit end of vessel 1B or somewhat short of it. The time on stream and the amount and kind of adsorbent employed in the beds is such that vessel 1A retains the entire amount of tertiary contaminants in the charge gas and vessel 1B receives the only the two remaining components of the initial feed mixture ($CH_4$ and hydrogen). The $CH_4$ is preferentially sorbed in 1B permitting substantially pure hydrogen to be recovered as the desired primary product through the manifold T.

2. At the end of step 1, flow communication between 1A and 1B is discontinued by closing valve 31 and the following operations carried out during the next time period of the cycle.

2a. High pressure rinse: A stream of essentially pure compressed secondary product ($CH_4$) at about the feed gas pressure from conduit Y is introduced into bed 1B in a direction same as that of the feed flow in step 1. Valves 51 and 81 are opened during this step and valve 91 is closed. The effluent gas from the bed is withdrawn through valve 81 and manifold S and recycled as feed to another A vessel than undergoing the adsorption step. The rinsing of bed 1B is continued until the said bed is saturated with methane at the feed gas pressure.

2b. Pressure Equalization: During part of the time while vessel 1B is undergoing the high pressure rinsing step (2a), the pressure in the companion vessel 1A is reduced by withdrawal of gas therefrom in a direction opposite to that of the earlier feed gas flow therein. This is accomplished by opening valve 101 to permit the withdrawn gas to flow into conduit W. The gas in conduit W is introduced into another selected A vessel, say vessel 3A, then at lower pressure than 1A, through valve 103 in a direction same as that of the initial feed flow.

2c. Depressurization: After step 2b, while bed 1B is still undergoing the high pressure rinse step (2a), bed 1A is further depressurized to substantially ambient pressure level. This is achieved by closing valves 101 and 103 and by opening valve 11. The desorbed gas from bed 1A during step constitutes part of the tertiary product gas and is withdrawn from the system through the conduit G. The direction of gas flow through 1A during this step is opposite to that of the initial feed flow.

3a. Depressurization. After step 2a vessel 1B is reduced in pressure to ambient level by withdrawal of gas therefrom in a direction opposite to that of earlier feed gas flow therein. Such withdrawal of gas is effected by controlled opening of the valves 61 and 31. Part of the withdrawn gas is fed to the compressor (C) through the manifold P and compressed to about feed pressure level before delivery to another B vessel, say vessel 2B, then undergoing the high pressure rinse step (2a). The remaining part of the withdrawn gas from bed 1B is used to purge vessel 1A through the control valve 31. The purging is done at near ambient pressure by dropping the pressure of the desorbed gas across valve 31.

3b. Purge. During the time period that 1B is undergoing step 3a, its companion vessel 1A is subjected to purging (rinsing) with part of the gas then being withdrawn from 1B. Such purge is effected in a flow direction opposite to that of the feed gas, through controlled opening of pressure reducing valve 31. The effluent gas from column 1A during the purge step is withdrawn through the conduit G as part of the tertiary product gas. Valve 11 is kept open during this step.

4a. Evacuation. Following step 3a, vessel 1B is evacuated to lowest pressure level of the cycle. This is accomplished in the embodiment illustrated by withdrawal of gas counter to the direction of feed gas flow by now opening valve 71 into vacuum line Q. Valve 31 and 61 are closed during this step. The evacuated gas may be directly discharged as secondary key product (methane) or, if needed, may be employed in part for further purging of vessel 1A. The extent of evacuation of the B vessels is governed by the purity of the primary product obtained in step 1. Optionally, evacuation of the B vessel can be effected by gas withdrawal at an intermediate level of the vessel.

4b. Optional purge. If further purging of 1A is required or desired following step 3b, such further purging is effected with gas being evacuated from 1B during step 4a. Thus the evacuated gas discharged at the outlet of vacuum pump V, or part of it, is admitted to conduit N. The gas can be admitted into the bed 1A by opening valves 21 and 41. The direction of this purge is also opposite to that of feed gas flow and it too, is carried out at near ambient pressure. The slight driving pressure necessary to flow the gas through bed 1A can be supplied by the compression of the vacuum pump. The effluent from column 1A during this purge step is also withdrawn as tertiary product gas through valve 11 and conduit G.

5a. Repressuring. The previously evacuated 1B vessel is now brought to feed pressure level by using part of the primary product gas from conduit T through reopened valve 91. During the initial time period that such repressuring of 1B is taking place valve 31 is in closed position. Valve 31 is subsequently reopened for gas flow into vessel 1A from 1B. The repressuring gas employed in this step is obtained from the effluent gas from another B vessel then on adsorption (step 1). The direction of gas flow into bed 1B during this step is opposite to that of the initial feed flow.

5b. Pressure equalization. During the first part of the time period during which vessel 1B is undergoing repressuring, its companion vessel 1A is brought to an intermediate pressure level by admission of gas thereto from conduit W through opened valve 101 in the direction of feed gas flow. The pressurizing gas is obtained from another A vessel, say vessel 4A, which is then undergoing step (2b). Valve 104 is opened to transfer this gas from vessel 4A into the manifold W from where it enters vessel 1A. When the pressure levels in vessels 1A and 4A become substantially equal, valves 101 and 104 are closed.

5c. Repressuring. Following step 5b, the vessel 1A is further pressurized to the feed pressure level by opening valve 31 and transferring some of the primary product gas from manifold T through valve 91 and vessel 1B. The time sequence and the flow rates are so arranged that the pressure level in vessel 1A at the end of step 5b is approximately the same as that of vessel 1B, at which time the valve 31 is opened.

6. With both vessels 1A and 1B now at feed gas pressure, valve 01 is again opened for start of a new cycle, beginning with step 1.

The operation taking place in each of the vessels during a complete operating cycle is outlined in Table 1 below. Generally, equal time duration is employed for each of the designated time period $0-t_1$, $t_1-t_2$ ... through $t_9-t_{10}$ in Table 1. A practical total cycle time for this process may be 20 minutes, each of the designed time period $0-t_1$, etc. in Table 1 being of 2 minutes duration. However, other cycle times may also be chosen.

While in the drawing the feed gas is shown as being introduced to flow downwardly through the A and B vessels, it will be understood that the initial feed, if desired, may be introduced to flow upwardly through these A and B vessels in that order. In that event, the direction of other gas flows will be changed to maintain the same relative directions with respect to the flow of the feed gas.

Table 1

| Vessels Cycle Time | Operation of Vessels | | | | | | | | | |
|---|---|---|---|---|---|---|---|---|---|---|
| | 1A | 1B | 2A | 2B | 3A | 3B | 4A | 4B | 5A | 5B |
| $0-t_1$ | A | A | PE | P | AR* | E | AR | D | PE | HR |
| $t_1-t_2$ | A | A | P | P | AR* | E | AR | D | D | HR |
| $t_2-t_3$ | PE | HR | A | A | PE | P | AR* | E | AR | D |
| $t_3-t_4$ | D | HR | A | A | P | P | AR* | E | AR | D |
| $t_4-t_5$ | AR | D | PE | HR | A | A | PE | P | AR* | E |
| $t_5-t_6$ | AR | D | D | HR | A | A | P | P | AR* | E |
| $t_6-t_7$ | AR* | E | AR | D | PE | HR | A | A | PE | P |
| $t_7-t_8$ | AR* | E | AR | D | D | HR | A | A | P | P |
| $t_8-t_9$ | PE | P | AR* | E | AR | D | PE | HR | A | A |
| $t_9-t_{10}$ | P | P | AR* | E | AR | D | D | HR | A | A |

A = Adsorption
D = Depressurization
PE = Pressure Equalization
E = Evacuation
P = Repressure
HR = High Pressure Rinse
AR = Ambient Pressure Rinse
* = Optional Table 2

| Time (Minutes) | VALVES | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 01 | 02 | 03 | 04 | 05 | 11 | 12 | 13 | 14 | 15 | 21 | 22 | 23 | 24 | 25 | 31 | 32 | 33 | 34 | 35 | 41 | 42 | 43 | 44 | 45 | 51 | 52 | 53 | 54 | 55 |
| 0-2 | 0 | | | | | | 0 | | | | | | | 0 | | 0 | | | | | | | | | | | | | | 0 |
| 2-4 | 0 | | | | | | 0 | 0 | | | | | | 0 | 0 | 0 | | | | | | | | | | | | | | 0 |
| 4-6 | | 0 | | | | | | 0 | | | | | | | 0 | | 0 | | | | | 0 | | | | | | | | |
| 6-8 | | 0 | | 0 | | | | 0 | | | | | | 0 | 0 | 0 | | | | | | 0 | | | | | | | | |

Table 2-continued

| | 61 | 62 | 63 | 64 | 65 | 71 | 72 | 73 | 74 | 75 | 81 | 82 | 83 | 84 | 85 | 91 | 92 | 93 | 94 | 95 | 101 | 102 | 103 | 104 | 105 |
|---|---|---|---|---|---|---|---|---|---|---|---|---|---|---|---|---|---|---|---|---|---|---|---|---|---|
| 8-10 | | 0 | | 0 | | | | | | | | | | 0 | 0 | | | | | | | | 0 | | |
| 10-12 | 0 | | | 0 | 0 | | | | | | | | | 0 | | 0 | 0 | | | | | | 0 | | |
| 12-14 | | | 0 | | 0 | | | | | | | 0 | | | | 0 | 0 | | | | | | | 0 | |
| 14-16 | | | 0 | | 0 | 0 | | | | | | 0 | | | | 0 | 0 | 0 | | | | | | 0 | |
| 16-18 | | 0 | | | 0 | | | | | | | | 0 | | | | 0 | 0 | | | | | | | 0 |
| 18-20 | | | 0 | | 0 | 0 | | | | | | | 0 | | | | 0 | 0 | 0 | | | | | | 0 |
| | 61 | 62 | 63 | 64 | 65 | 71 | 72 | 73 | 74 | 75 | 81 | 82 | 83 | 84 | 85 | 91 | 92 | 93 | 94 | 95 | 101 | 102 | 103 | 104 | 105 |
| 0–1 | | | 0 | | 0 | | | | | | | | | 0 | 0 | 0 | | | | | | 0 | | | 0 |
| 2–4 | | | 0 | | 0 | | | | | | | 0 | 0 | 0 | | | | 0 | | | 0 | | 0 | | |
| 4–6 | | | | 0 | | 0 | | | 0 | 0 | | | | | | | 0 | 0 | | | 0 | | 0 | | |
| 6–8 | | | | 0 | | 0 | | | 0 | 0 | | | | | | | 0 | 0 | | | | | | | |
| 8-10 | 0 | | | | | | | 0 | 0 | | | | | | | | 0 | 0 | | | | 0 | | | 0 |
| 10-12 | 0 | | | | | | | 0 | 0 | | | | | | | | 0 | 0 | | | | | | | |
| 12-14 | | 0 | | | | | | 0 | | | 0 | | | | | | 0 | 0 | | | | 0 | | | 0 |
| 14-16 | | 0 | | 0 | | | | | | | 0 | | | | | | 0 | 0 | | | | | | | |
| 16-18 | | 0 | | 0 | | | | | | | | | 0 | 0 | | | 0 | 0 | | | 0 | | | | |
| 18-20 | | 0 | | 0 | | | | | | | | 0 | 0 | | | | | 0 | | | | | | | |

0 = OPEN
BLANK = CLOSED

Table 2 indicates the positions of the valves during a complete cycle. The arrangement is applicable for the case where the optional purging of the A beds with the evacuated gas from the B beds is not required. In Table 2 an artibrarily selected 20 minute time cycle is illustrated. It will be understood that a longer or shorter time period could be employed.

While the invention has been particularly described in connection with the separation and recovery of hydrogen as the primary key component and methane as the secondary key component from a multicomponent gas mixture containing these accompanied by $C_2+$ hydrocarbons as dilute tertiary contaminants, it will be understood that the described system and operation can be advantageously employed in the separation of contained components of other multicomponent gas mixtures having present therein (1) a major portion of a primary key component which is not substantially adsorbed in the first or second adsorbent bed of the train, (2) secondary key component present in bulk concentration and which is preferentially absorbed relative to the primary key component in the second adsorbent bed, and (3) one or more dilute tertiary components which are selectively adsorbed with respect to both primary and secondary components in the first adsorbent bed.

Any sorbent which is selective for the diluent component(s) may be employed in the first beds (A) of the train and any sorbent selective for the secondary key component can be used in the subsequent (B) adsorbent beds. Thus for the multicomponent gas mixture illustrated wherein the feed gas mixture contains hydrogen, methane and $C_2+$ hydrocarbons, the A vessels may contain as adsorbent BPL activated carbon, MSC-V coke or RB activated carbon; while the B vessels may contain MSC-V coke, BPL activated carbon or 5 A° molecular sieves as adsorbent. In general, the choice of the particular sorbent is governed by the operating conditions (such as temperature and pressure) employed in the separation process and the composition of the feed gas mixture and the nature of the impurities sought to be removed as well as by the quality of the product gases required.

EXAMPLE

The ten bed embodiment of the invention as illustrated in FIG. 1 will be more fully understood by the following example:

The system consists of five A beds, each packed with 12 lbs (5.44 Kg) of RB activated carbon, and five B beds each packed with 50 lbs (22.7 Kg) of MSC-V coke. A feed gas comprising 72.0% $H_2$, 20.0% $CH_4$, 5.0% $C_2H_6$ and 3.0% $C_3H_8$ (by volume) at 441 psia (30.41 bars) and at a temperature of 86° F. (30° C.) is introduced into one of the A columns connected in series with one of the B columns, both of which are previously pressurized to the feed gas pressure level. The feed flow rate is 4.0 lb moles/hour (1.8 Kg moles/hr). A stream of hydrogen containing 99.5+% $H_2$ (by volume) is withdrawn through the exit end of the B column. A part of this stream is withdrawn as product $H_2$ at a rate of 2.68 lb moles/hour (1.2 Kg moles/hr).

The adsorption step is continued for four minutes after which the feed is switched to another A column. The interconnecting valve between the A and the B columns is then closed and the A column is pressure equalized by connecting it with another A vessel which is previously rinsed at near ambient pressure level. The pressure in the two A columns at the end of the pressure equalization step is about 229 psia (15.7 bars). The A column is then further depressurized to near ambient pressure level in two minutes and the desorbed gas is withdrawn from the A column as the tertiary product gas. While the A column is undergoing the pressure equalization and the depressurization steps, the B column is rinsed with a stream of essentially pure $CH_4$ at about 442 psia (30.47 bars) pressure level. The rinse step is continued until the whole of the B column is saturated with $CH_4$ at about 442 psia. This step is carried out for four minutes and the effluent from the B column during this time is recycled as feed by mixing it with fresh feed gas into another A column then undergoing the adsorption step. At the end of the high pressure rinse step, the B column is depressurized to near ambient pressure level in four minutes. Part of the desorbed gas from the B column, comprising of essentially pure $CH_4$, is recompressed and recycled as the high pressure rinse gas into another B column then undergoing the high pressure rinse step. The rest of desorbed $CH_4$ is used to purge the companion A column at near ambient pressure. The effluent from the A column during this time is withdrawn from the system as tertiary product gas. The combined flow rate of the tertiary product gas obtained from this step and from the previous depressurization step of the A column is 0.99 lb moles/hour (0.45 Kg moles/hr). The composition of the mixed tertiary product gas is 47.5% $CH_4$, 20.2% $H_2$, 20.2% $C_2H_6$ and 12.1% $C_3H_8$ (by volume).

At the end of the depressurization step, the column B is evacuated from near ambient pressure to a level of 1.5 psia in four minutes. The desorbed $CH_4$ from this step is withdrawn as the secondary key component product comprising of 99.9+% $CH_4$ (by volume). The flow rate for the secondary product is 0.33 lb moles/hour (0.15 Kg moles/hr).

At the end of the evacuation step, the column B is pressurized to about 228 psia (15.7 bars) in two minutes with a portion of the primary component product gas withdrawn from another B vessel then undergoing the adsorption step. During the same time, the companion A vessel is pressure equalized with another A vessel then undergoing the initial depressurization step. Finally, both A and B vessels are pressurized from about 228 psia to about the feed pressure level in two minutes by flowing a portion of the primary product gas thereinto. The interconnecting valve between the A and the B vessels is opened during this step. The beds are now ready to undergo another cycle of operation according to the scheme of the embodiment.

As a consequence of this operation, the feed gas is fractionated into a primary product comprising of 99.5+% $H_2$ with a hydrogen recovery from the feed gas of about 93.1% and a secondary product comprising 99.9+% $CH_4$ with a methane recovery from the feed gas of about 41.2% and a tertiary product comprising 47.5% $CH_4$, 20.2% $H_2$, 20.2% $C_2H_6$ and 12.1% $C_3H_8$ by volume.

What is claimed is:

1. In the separation of a multicomponent feed gas mixture in a system comprising a plurality of first and second sorbent beds, with the individual recovery of a primary key component and a secondary key component present in such mixture, by selective sorption, wherein said secondary key component is more strongly sorbed by the sorbent employed than the primary key component and there is present in said mixture at least one other tertiary gas component, which is present in dilute concentrations and which is more strongly sorbed than both the primary key and the secondary key component; the method which comprises in an adiabatic pressure swing cycle the sequential steps of
   (a) an adsorption step during which such multicomponent feed gas mixture at initial superatmospheric pressure is passed through a first sorbent bed selective for preferential retention of tertiary gas component(s) and then through a second sorbent bed selective for retention of said secondary key component, and discharging from said second sorbent bed unadsorbed primary key component, said passing of the multicomponent gas mixture being continued for a controlled time period until or short of breakthrough of said secondary key component from said second sorbent bed, while retaining essentially all of the tertiary gas component(s) in said first adsorbent bed;
   (b) thereafter interrupting feed gas flow to said first bed and discontinuing gas flow communication between said first and second beds; and
      (i) rinsing said second sorbent bed at about initial feed pressure by flowing a stream of essentially pure secondary product gas component therethrough until said second bed is saturated with said secondary component; and meanwhile
      (ii) first reducing to an intermediate level the pressure in said first bed by gas withdrawal therefrom, and
      (iii) then further reducing the pressure in said first bed to substantially ambient level by further gas withdrawal therefrom, and;
   (c) thereafter, reducing the pressure of the said second bed to substantially ambient pressure level by gas withdrawal therefrom comprising substantially pure secondary key component, and during such pressure reduction of said second bed
      (i) purging said first bed with part of the gas being withdrawn from said second bed; and
      (ii) purging another second bed, which is then undergoing the high pressure rinse step defined in (b), with part of the gas being withdrawn from the first mentioned second bed after compressing the said withdrawn gas to about the initial feed pressure;
   (d) following reduction of pressure in said second bed to substantially ambient pressure level, evacuating said bed to lowest pressure in the operating sequence thus further desorbing secondary key component therefrom; and
   (e) repressuring the previously evacuated second bed to feed pressure level by flow thereinto of primary product gas and while said second bed is being thus repressured,
      (i) first bringing said first bed to an intermediate pressure level by flow thereinto of a gas stream comprising the desorbed gas from another first bed then undergoing the pressure reduction step defined in step (b), and
      (ii) then re-establishing flow between said second and first beds and flowing primary product gas through said second bed into said first bed until said first bed is brought to initial feed gas pressure level, and
   (f) when said first and second beds are at feed gas pressure at the conclusion of step (e) above, repeating the above-recited sequence of operations beginning with step (a) above.

2. The method as defined in claim 1 wherein said multicomponent feed gas mixture comprises hydrogen as the primary key component, methane as the secondary key component and $C_2+$ hydrocarbons as the tertiary components.

3. The method as defined in claim 2 wherein a carbonaceous solid adsorbent is employed in at least said first bed.

4. The method as defined in claim 1 wherein the separation of the multicomponent gas mixture is effected in a system comprising a plurality of such first sorbent beds operated sequentially in parallel and a plurality of such second sorbent beds each of which is selectively coupled in series with a selected one of said first beds at least during passage of the feed gas mixture into such selected first bed.

5. The method as defined in claim 4 wherein said rinsing of the second sorbent bed at about the feed gas pressure is effected by gas flow in the same direction as that of initial flow of the feed gas mixture thereinto.

6. The method as defined in claim 5 wherein at least a portion of the effluent gas from said second bed during the high pressure rinse step is recycled for admixture with the multicomponent feed gas being charged for separation of its components.

7. The method as defined in claim 4 wherein the recited pressure reduction of said first bed is effected by withdrawal of gas therefrom in a flow direction opposite to that of initial feed gas flow therein.

8. The method as defined in claim 7 wherein at least part of the effluent gas withdrawn from said first bed is sent to another first bed of the system then at lower pressure to equalize the pressure between said first beds.

9. The method as defined in claim 4 wherein part of the effluent gas withdrawn during the pressure reduction of the said first bed is removed from the system as the tertiary product gas.

10. The method as defined in claim 4 wherein the recited pressure reduction of said second bed is effected by withdrawal of gas therefrom in a flow direction opposite to that of the initial feed flow.

11. The method as defined in claim 10 wherein at least a portion of the desorbed gas from the said second bed is recompressed to about the initial feed pressure level and used as the high pressure rinse gas into another second bed.

12. The method as defined in claim 10 wherein at least a portion of the desorbed gas from the said second bed is used as purge gas into a first bed.

13. The method as defined in claim 12 wherein the direction of purge gas flow through the said first bed is opposite to that of initial feed flow therein, and the effluent from the said first bed during the purge step is withdrawn from the system as the tertiary product gas.

14. The method as defined in claim 4 wherein evacuation of said second bed is effected by removal of gas therefrom in a direction opposite that of initial feed gas flow therein.

15. The method as defined in claim 14 wherein at least a portion of the gas evacuated from the said second bed is employed in purging said first bed.

16. The method as defined in claim 14 wherein a portion of the gas evacuated from the said second bed is withdrawn from the system as the secondary key product gas.

17. The method as defined in claim 4 wherein the second bed is repressured with the primary key product gas to the initial feed pressure level after the evacuation step by gas flow thereinto in a direction opposite to that of the initial feed gas flow therein.

18. The method as defined in claim 17 wherein the said primary product gas used for repressuring the said second bed comprises part of the primary product gas then being produced by another second bed which is then undergoing the adsorption step.

19. The method as defined in claim 4 wherein said first bed is brought to intermediate pressure level following the recited purging thereof, by flow of gas thereinto in the same direction as that of the initial feed gas flow therein.

20. The method as defined in claim 19 wherein the said first bed is pressurized to an intermediate pressure level by flowing thereinto the desorbed gas from another first bed then undergoing the depressurization step (b), thus pressure equalizing the two first beds.

21. The method as defined in claim 20 wherein the said first bed, following the recited pressure equalization step, is brought to initial feed pressure level by connecting said first bed in series with a second bed and flowing a portion of the primary product gas through said second bed and into said first bed.

22. The method as defined in claim 21 wherein the direction of the primary product gas flow into the said first bed is opposite to that of the initial feed flow therein.

* * * * *